(12) United States Patent
Franzini et al.

(10) Patent No.: US 9,146,448 B2
(45) Date of Patent: Sep. 29, 2015

(54) CORRELATED CONTROL FOR CLOSE FOCUS STEREOSCOPIC VIEWING

(71) Applicants: John Franzini, Hollis, NH (US); Matthew Robichaud, Lowell, MA (US)

(72) Inventors: John Franzini, Hollis, NH (US); Matthew Robichaud, Lowell, MA (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 266 days.

(21) Appl. No.: 13/948,526

(22) Filed: Jul. 23, 2013

(65) Prior Publication Data

US 2014/0021352 A1 Jan. 23, 2014

Related U.S. Application Data

(60) Provisional application No. 61/674,432, filed on Jul. 23, 2012.

(51) Int. Cl.

| | | |
|---|---|---|
| G02B 23/00 | (2006.01) |
| G03B 15/14 | (2006.01) |
| H01L 27/146 | (2006.01) |
| G02B 23/12 | (2006.01) |
| G03B 17/48 | (2006.01) |
| G02B 7/06 | (2006.01) |
| G02B 23/18 | (2006.01) |
| A61B 5/00 | (2006.01) |
| H04N 5/225 | (2006.01) |
| H04N 5/33 | (2006.01) |
| H04N 13/02 | (2006.01) |
| H04N 13/04 | (2006.01) |

(52) U.S. Cl.
CPC .............. *G03B 15/14* (2013.01); *A61B 5/0068* (2013.01); *A61B 5/489* (2013.01); *G02B 7/06* (2013.01); *G02B 23/12* (2013.01); *G02B 23/18* (2013.01); *G03B 17/48* (2013.01); *H01L 27/14625* (2013.01); *H04N 5/2251* (2013.01); *H04N 5/33* (2013.01); *H04N 13/0239* (2013.01); *H04N 13/0402* (2013.01)

(58) Field of Classification Search
None
See application file for complete search history.

(56) References Cited

U.S. PATENT DOCUMENTS

| 6,701,081 | B1 | 3/2004 | Dwyer et al. | |
|---|---|---|---|---|
| 2002/0079425 | A1* | 6/2002 | Rhoads | 250/201.9 |
| 2012/0218387 | A1* | 8/2012 | Aoki et al. | 348/47 |

* cited by examiner

*Primary Examiner* — Arnel C Lavarias
(74) *Attorney, Agent, or Firm* — Hayes Soloway P.C.

(57) ABSTRACT

Exceptionally crisp infrared images are provided by a binocular infrared imaging system for close in focusing that simultaneously directs the center lines of the optical channels to a close in point while at the same time providing auto focusing.

18 Claims, 6 Drawing Sheets

CORRELATED CONTROL FOR CLOSE FOCUS STEREOSCOPIC VIEWING

STATEMENT OF GOVERNMENT INTEREST

The invention was made with United States Government support under Contract No. H94003-04-D-002/0076 awarded by the US Army. The United States Government has certain rights in this invention.

RELATED APPLICATIONS

This application claims rights under 35 USC §119(e) from U.S. Application Ser. No. 61/674,432 filed Jul. 23, 2012, the contents of which are incorporated herein by reference.

FIELD OF THE INVENTION

This invention relates to stereoscopic and more particularly to an infrared system for close in infrared imaging, especially of the human body so that ultra-sharp stereoscopic images of a region on the body may be presented.

BACKGROUND OF THE INVENTION

In phlebotomy and other medical procedures it is oftentimes important to be able to see subsurface structures in order to better perform a surgical operation or for instance to locate veins in order to successfully complete a phlebotomy.

In the past infrared imaging in the medical environment to detect bleeding and arterial structure and for instance anything that cannot be seen in the visible region of the electromagnetic spectrum such as bone overheating, tissue overheating and the like cannot be readily observed due to the lack of the ability of instruments to provide a reasonably sharp infrared image of the inspected area.

Moreover, focal plane arrays for infrared imaging in the past have only been available with 28 micron pixel spacing which does not lend itself to anything other than a relatively fuzzy picture of the body part being inspected by the thermal imagery process.

Typically thermal imaging on the body has involved long wave infrared in the range of 8-15 µm. However with 28 micron pixel spacing image quality remains poor.

Moreover, those thermal imaging instruments that are utilized in the medical field could only focus from infinity down to 10 meters or perhaps as little as 1 meter.

However, those IR imaging systems that were capable of 1 meter focal lengths were not useful in close up viewing of the human body that require a 6 inch to 60 inch operating range. Thus, while microbolometers have been used to detect heat, the only thing that was sensed was an average heat reading over a given area. Thus, short range thermal imaging only resulted in fuzzy or blurry images. In short, these devices could not focus close in on subjects.

One of the reasons for the failure of IR imagers to have a very short focus was in part due to the size of the optics and the hardware necessary to provide a close in sharp image. It will be appreciated that providing a blotchy image of a human body part or area is not very useful in detecting subsurface structure.

Regardless of the fact that there were no single optical channel systems to produce sufficiently sharp infrared images, there was still a need for stereo imagery in certain surgical procedures to provide depth perception. Depth perception is oftentimes important because when doing surgery one can accidently for instance cut an adjacent structure so that for instance blood vessels could be nicked during the procedure. Without depth perception one could not identify the location of the internal structure. Thus in the prior art there were no stereo infrared imaging systems used, much less those capable of imaging targets within about 6 inches of the objective lenses of the binoculars. The requirement therefore is to have acceptably sharp thermal images for objects within 6 to 60 inches from the objective lenses of the binocular viewing device, a requirement not met by current infrared technology.

Referring to U.S. Pat. No. 6,701,081 a binocular system is described which enables focusing to a point in space removed from the objective lenses by skewing the optical center lines of the optical channels so that they converge on a spot somewhere short of infinity. Note that the system operates in the visible region of the electromagnetic spectrum and was not used for thermal imaging. Moreover, from this patent it appears that the minimum focus distance was on the order of 10 feet which would make it inapplicable to the type of medical imaging described above.

However, just simply having the two optical channels having optical center lines which intersect at a distance from the binoculars is not sufficient to provide crisp focusing. The only way to provide crisp focusing is by providing a focal plane array spaced from an objective lens and by moving the focal plane array relative to the objective lens.

It will be appreciated that both skewing the optical channels to intersect at a close-in range as well as providing independent focusing for each of the channels once the channels have been skewed would provide for the best resolution of a close in image.

It is noted that the above-mentioned patent uses a worm gear to rotate the optical axes of the two channels of the binoculars, and involves a relatively long focus distance incompatible with short close in work that would be required in the medical field, namely a 6 to 60 inch working distance.

Moreover, any movement of the image focal plane in the two channels of the above-mentioned patent is restricted to adjusting the image focal plane in one channel to be exactly at the same distance as the image focal plane of the other channel, there being no independent adjustment of the focal planes in each channel and certainly no automatic focus involving the movement of focal plane arrays in each of the channels relative to their own objective lenses.

SUMMARY OF INVENTION

In order to provide exceptionally crisp infrared images for instance for use in biomedical applications, a binocular infrared imaging system for close in focusing simultaneously provides for a close in focal point and simultaneous focusing in each of the optical channels. To do this a mechanism is provided for skewing the center lines of the two optical channels in the binocular to intersect at a close in point while simultaneously adjusting the distance of the focal plane arrays in each of the channels from their respective objective lenses. The result is that in one operation the focal point of the binoculars is moved in towards the binoculars while at the same time adjusting focal plane array positioning for precise focusing in each of the channels. The subject binocular infrared imaging system provides images of such crispness and sharpness that the subject infrared imaging system may be utilized for close in work in the medical field such as for instance in surgery and phlebotomy applications.

More particularly, in order to be able to provide exceptionally sharp or crisp thermal imaging for medical applications and the like in which subsurface characteristics are made viewable with sufficient sharpness, an infrared binocular arrangement includes the ability to have the optical center lines of the two optical channels intersect at a point as little as 6 inches from the objective lenses of the binoculars to as much as 60 inches, thus to provide exceptionally sharp close in thermal image viewing. Simultaneous with the adjustment or skewing of the two optical center lines, the focal plane arrays in each of the channels are focused either mechanically or electronically such that not only are the optical center lines of the channels coincident directly at the point to be imaged, but also the focal plane arrays associated with each of the channels are independently adjusted so that exceptional stereo infrared clarity is achieved.

In order to support increased resolution of the close in infrared system, focal plane arrays having 17 micron pixel spacing are used.

In one embodiment, the two optical channels are pivotable around two different pivots utilizing sector gears that are activated by a focusing distance gear, rotated by a focus knob and positioned in between the sector gears. The sector gears are moved by the focusing distance gear so as to make the optical center lines of the two channels coincident on a point in space within the 6 inch to 60 inch working distance.

In one embodiment, a pin slot actuating system is utilized such that when the sector gears are moved to skew the optical center lines, the focal plane arrays associated with each of the two channels are moved due to the camming action of the pin slot measurement to vary the distance between the focal plane array and its associated objective lens. Thus, as the optical axes of the two channels are skewed inwardly, each focal plane array is moved away from its objective lens by the appropriate amount to maintain sharp focus.

The focal plane arrays are arranged on translating carriage assemblies which are supported in one embodiment by rods running aft from the lens support assembly from the associated objective lens so that the carriage is always moved along the center line of its objective lens. In another embodiment a wheel and track assembly is utilized in which the carriage, rather than being suspended on rods is translated in a track using the wheel track assembly, again maintaining the focal plane movement along the center line of the associated objective lens.

In combination with the camming action for positioning the focal plane arrays, in one embodiment each of the carriages carries an auto focus assembly which can be utilized either separately or in addition to the focusing accomplishable by the above camming action when focusing on a particular point within the working range.

The results of the two actions provide a clear image of underlying thermal structures such as for instance in phlebotomy the ability to resolve even the thinnest of veins. When used in phlebotomy the subject binocular device is mounted above the arm or leg to be phlebotomized. A 3D display driven by the focal point arrays provides the technician with a clear accurate picture of where the subsurface veins are and the ability to be able to insert a needle at the exact point where the vein occurs. Unlike monocular systems, binocular infrared optics allow depth perception to assure proper placement of surgical instruments.

The subject infrared binocular system may be used not only for phlebotomy but also in many types of surgical procedures where it is important to be able to resolve artifacts or structures that are obscured by other tissue. So good is the infrared imagery that it rivals that of imagery in the visible region of the electromagnetic spectrum to give doctors and surgeons a new tool in performing precise surgeries that heretofore may have resulted in accidental nicks or cutting of unwanted structures within the body.

In summary, in order to obtain exceptional sharpness for infrared images the two optical channels need to be pointed at the same near in point in space both horizontally and vertically. Note that in azimuth the eyeballs are able to correct a large degree of error. But if the two channels are not perfectly aligned in azimuth or horizontally then the person's eyes can go cross-eyed which is not comfortable. With respect to elevation or height error if the point of focus is off, the person utilizing the binocular system will get headaches because the individual cannot fuse the two images together. Elevation error is minimized by shimming.

BRIEF DESCRIPTION OF THE DRAWINGS

These and other features of the subject invention will be better understood in connection with the Detailed Description, in conjunction with the Drawings, of which.

DETAILED DESCRIPTION

Figure 1:
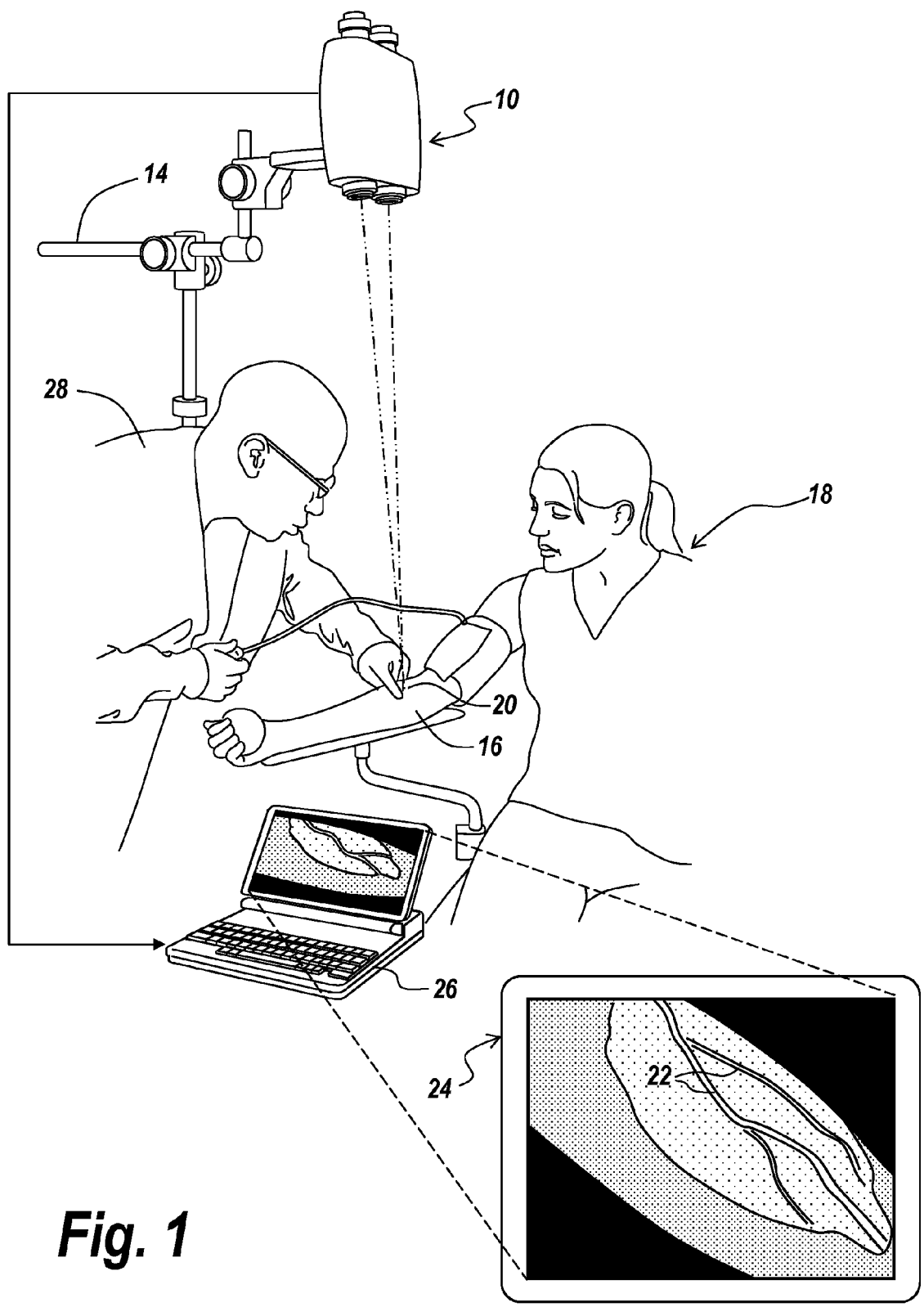
FIG. 1 is a diagrammatic illustration of the utilization of the subject binocular infrared system for identifying blood vessels in the arm of a patient undergoing a phlebotomy.

Referring now to FIG. 1, a binocular infrared imaging system 10 is located by a support apparatus 14 above the arm 16 of a patient 18 so that the point of focus of the binocular is at a point 20 on the arm of the patient.

The purpose of providing such an infrared imaging device is to be able to locate subsurface structures in the arm in this case for the purpose of a phlebotomy, in which the subsurface structures to be detected are the veins 22 in arm 16 as projected onto a display 24 when using for instance a computer laptop 26 coupled to the focal plane arrays of the binocular device. It will be appreciated that FIG. 1 is for illustrative purposes to show that the image developed by the infrared binocular is exceedingly crisp and sharp. It will be noted that display 24 may be a three dimensional display for providing depth perception. Alternatively individual LCD displays may be mounted in the eyepieces of the binoculars, with the small LCD displays driven by the focal plane arrays. As a result peering into the binoculars provides the crisp 3D image available from the subject unit.

It will also be appreciated that rather than mounting binocular 10 on a support device 14 above a physician 28's head, the support device may support binoculars 10 at a position usable by doctor 28 to view the binocular image directly from the binoculars, with the binoculars positioned between the doctor's head and arm 16 of the patient.

In either case a binocular view of the point 20 on the patient's arm is viewed in three dimensions because of the stereoscopic view associated with binoculars 10.

In order to provide for a crisp image to be viewed by the doctor or other personnel performing the surgical procedure it is of paramount importance to be able to crisply represent to the doctor or other personnel the subsurface structure on which the doctor or other personnel are operating. It is thus the purpose of the subject binocular infrared imaging system to give the doctor or other medical personnel the ability to visualize subsurface structures and to be able to position scalpels or other operating equipment relative to the subsurface structure without for instance nicking or otherwise damaging surrounding structure. This for instance provides the doctor or other medical personnel the ability to visualize the subsurface structure not only for instance in locating veins for a phlebotomy procedure but also for instance to locate bone structure beneath soft tissue when an operation so requires. Thus the subject infrared binocular system is useful for instance in knee surgery and in a large number of other surgeries in which the object to be operated on is hidden by tissue which would obstruct the subsurface structure.

In one embodiment the binocular infrared imaging system utilizes long wave, infrared radiation which is particularly useful in detecting subsurface structures due to the heat that the subsurface structure exhibits or radiates.

Figure 2:
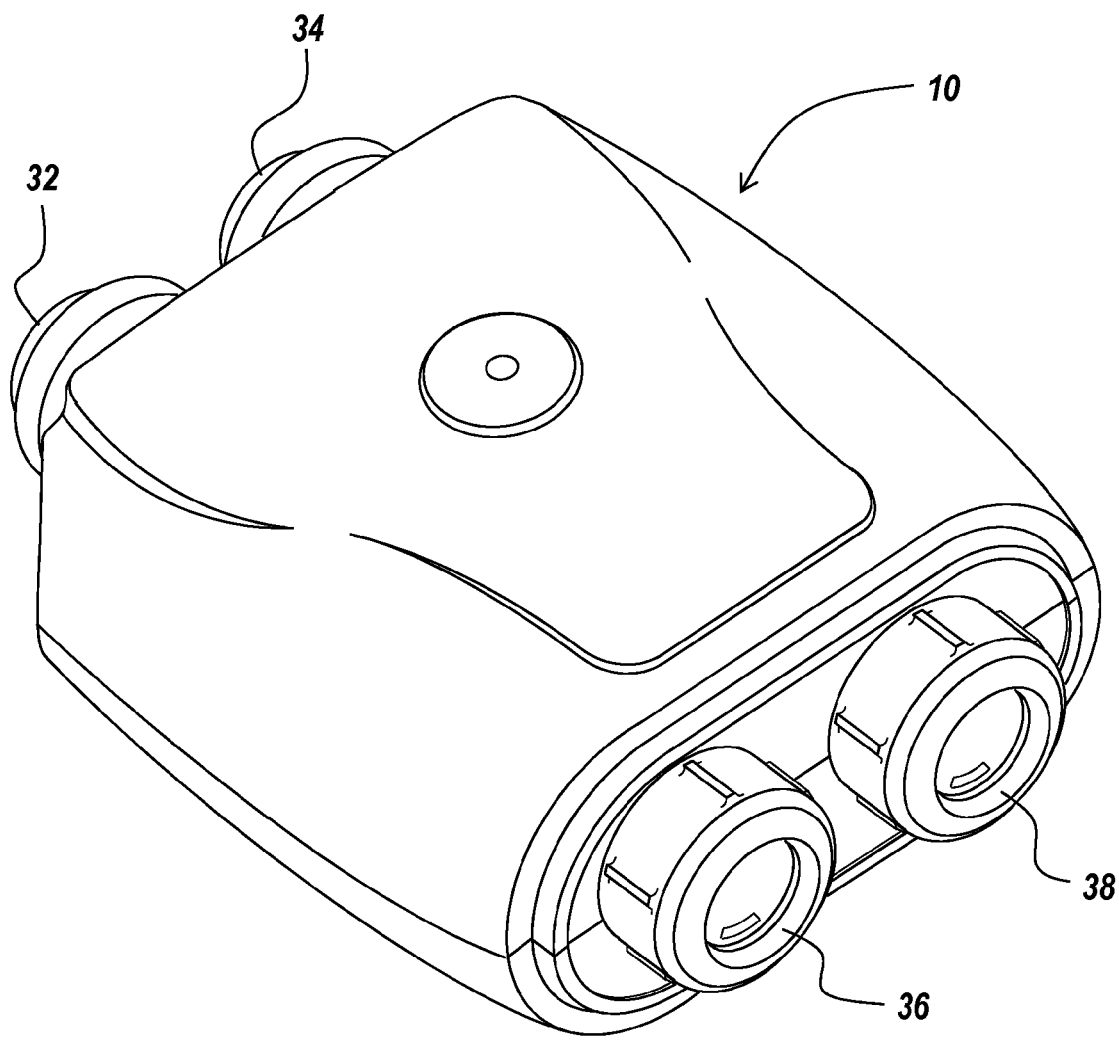
FIG. 2 is a diagrammatic illustration of the infrared binocular housing used for the binocular instrument of FIG. 1.

Referring to FIG. 2, the subject binocular infrared imaging system includes the binoculars which have two optical channels with eye piece and lenses 32 and 34 providing one end of the optical channel with objective lenses 36 and 38 providing the other end of the optical channel.

Figure 3:
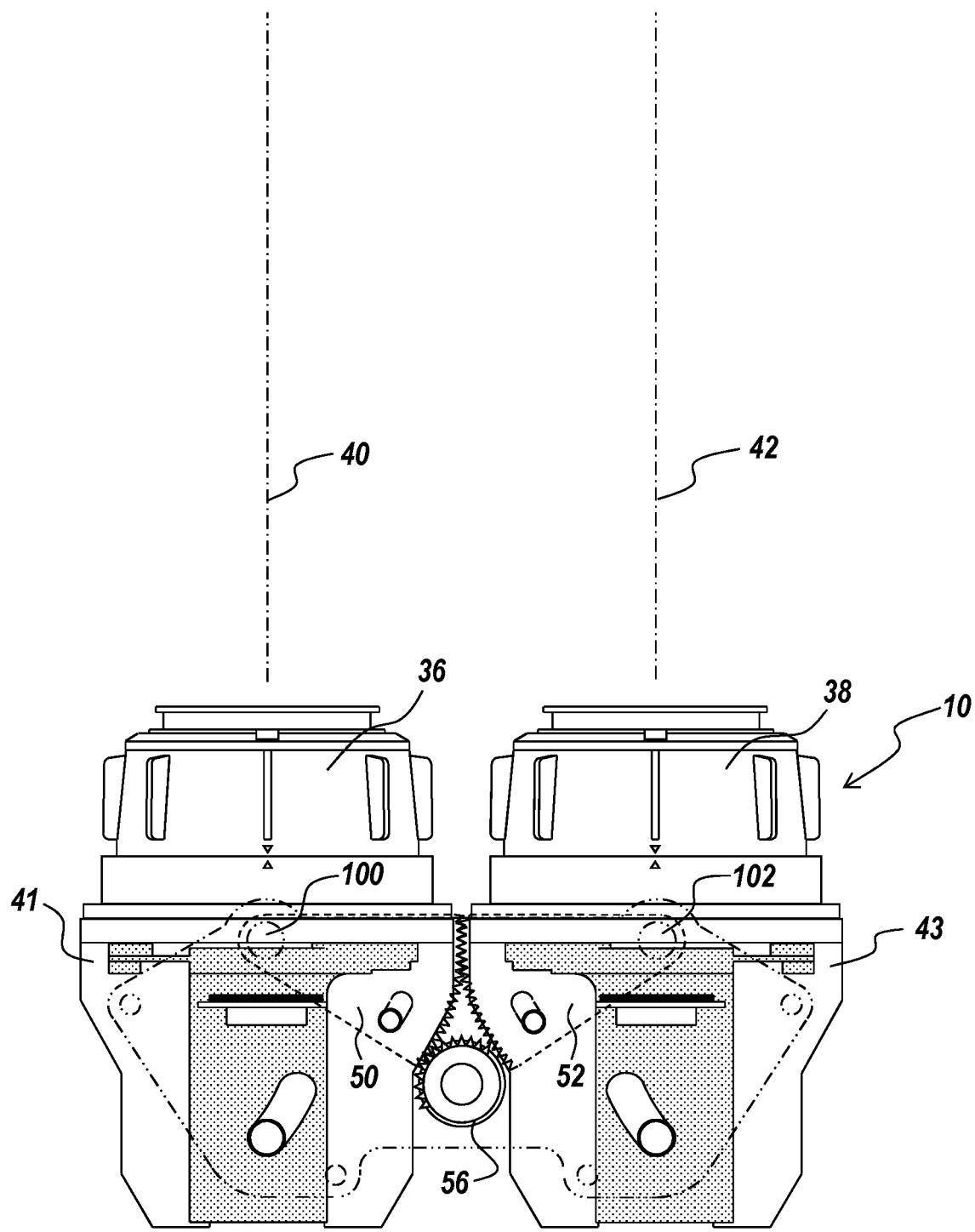
FIG. 3 is a diagrammatic illustration of the optical channels in the binocular of FIG. 2 illustrating that the binocular channels are focused at infinity with the drawing sectors for each of the channels being such as to provide that the channel optical axis are parallel.

Initially the binocular 10 has the optical channels parallel and focused at infinity, as illustrated in FIG. 3, in which the optical center lines 40 and 42 for the two optical channels are parallel. Each of the objective lenses 36 and 38 are supported on a pivotable lens support assembly 41 and 43 which is pivoted around respective pivot points 100 and 102. Note that the pointing direction of each of the optical channels is determined by the position of sector gears 50 and 52 whose positions are in turn dictated by a focus gear 56 which is operated by a focusing knob to move the direction of center lines 40 and 42 to cross as illustrated in FIG. 4 at a point 56 which is within a working range of 6 inches to 60 inches, thereby to provide for close in imaging such as useful in medical applications.

Figure 4:
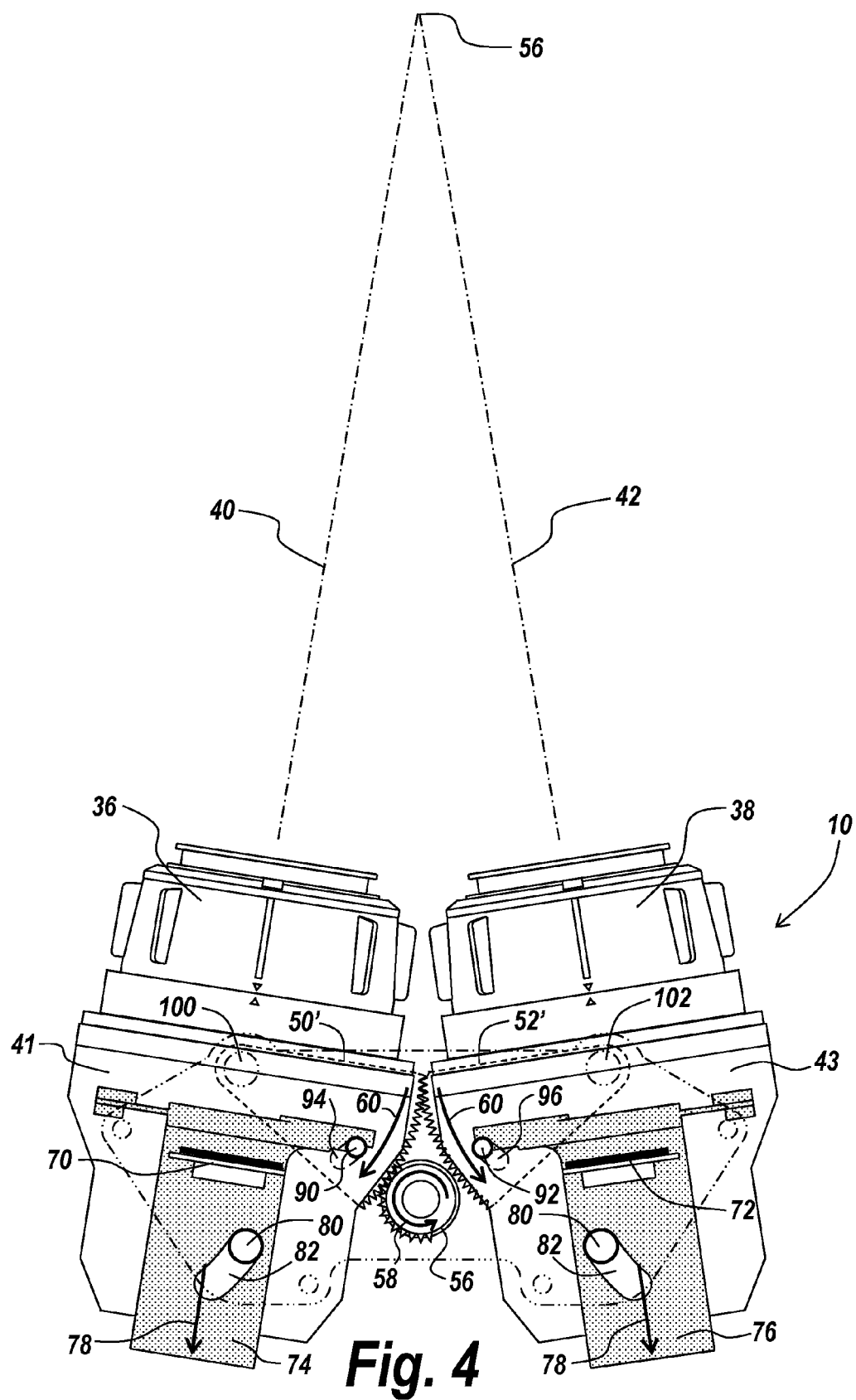
FIG. 4 is a diagrammatic illustration of the optical channels of FIG. 3 showing the skewing of the optical channels to focus on a point between 6 and 60 inches from the binoculars through the utilization of the drive sector skewing arrangement which moves the channels to intersect at a point close to the binoculars and with a mechanical drive utilized to move the focal plane arrays in each of the channels away from the principal optics as the skewing increases thus to maintain proper focusing on the close in point.

In order to achieve the crispness of infrared imaging, and referring now to FIG. 4, it will be seen that center lines 40 and 42 are skewed so as to cross at point 56. This is accomplished by rotation of gear 56 in the direction of arrow 58 which causes sectors 50 and 52 to move in the direction of arrows 60 so as to come to rest at the position shown at 50' and 52'. This action in and of itself causes the lens support assembly 41 and 43 to shift the optical channels so as to skew them onto a close in point. This is because sectors 50 and 52 are mechanically connected to the lens support assemblies for the optical channels.

Being able to skew the optical axis of the two channels onto a close in point will improve the focus by which the infrared objects may be viewed. It is nonetheless important to be able to simultaneously adjust focal plane arrays 70 and 72 relative to their objective lenses 36 and 38.

In order to do this, each of the focal plane arrays is mounted to a translatable carriage 74 and 76 which are made to move in the direction of arrows 78 in an aft direction along the center line of each of the associated objective lenses. Thus, as the focal point 56 moves towards the binocular system the focal plane arrays are moved aft along the center line to maintain focus of point 56 onto the respective focal plane array.

How this mechanical focusing system moves carriages 74 and 76 is now described. In each case a pin 80 fixed to the binocular body coacts with a corresponding slot 82 in carriages 74 and 76 such that as the direction of the optical channels are skewed, the action of the fixed pin 80 against the slot in the carriage moves the carriage aft from the position shown in FIG. 3 to the position shown in FIG. 4, with the fixed pin moving from one end of the slot 82 to the other as the skewing angle is increased.

It will be appreciated that the movement of sectors 50 and 52 moves the objective lens support assembly 41 and 42. Here it will be noted that sectors 50 and 52 are constrained in their motion by fixed pins 90 and 92 cooperating with associated slots 94 and 96. Thus, the sector movement is mechanically ganged to the objective lens support assembly of the optical channels so as to provide the aforementioned skewing.

Figure 5:
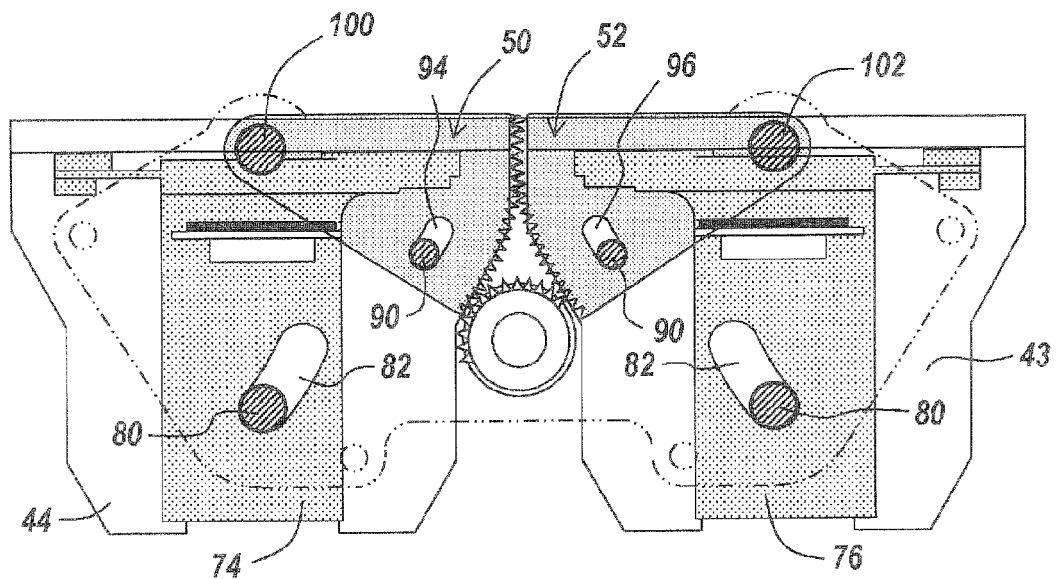
FIG. 5 is a diagrammatic top view of the sector skewing apparatus and the apparatus involved in the placement of the focal plane array at the appropriate distance from associated principal lenses with movement of the carriage carrying the focal plane arrays accomplished in a pin cam arrangement.
Figure 6:
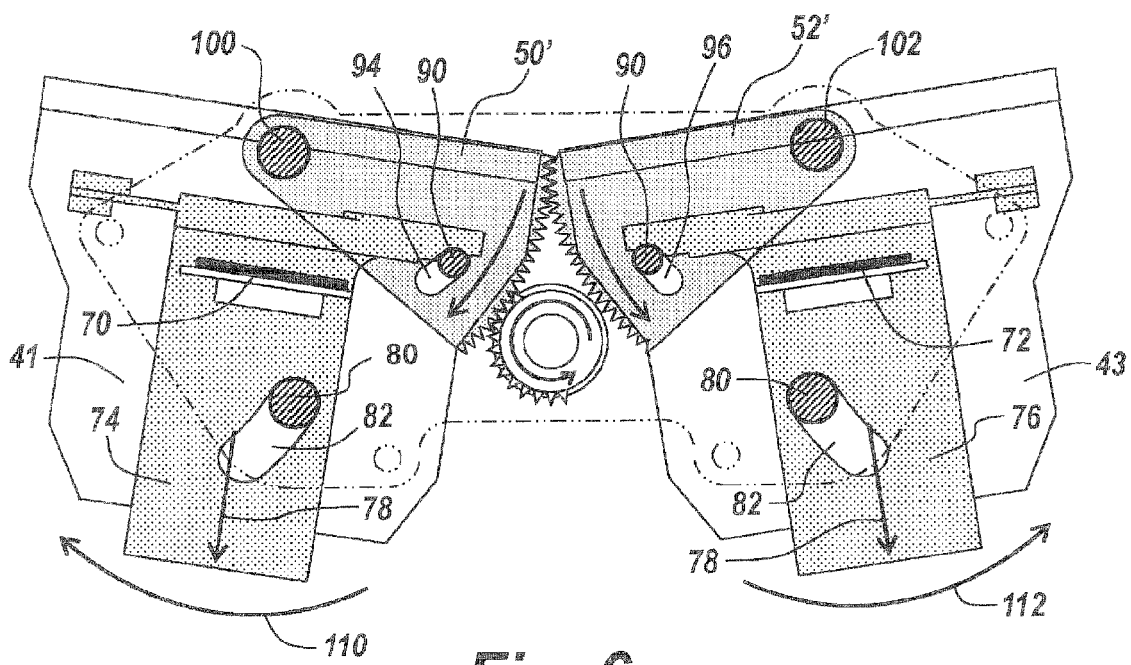
FIG. 6 is a diagrammatic illustration of the arrangement of FIG. 5 in which the channels are skewed by the movement of the sector gears which in turn cams the carriage for the focal plane arrays aft along the center line of each of the optical channels simultaneously with the skewing.

This action is more clearly shown in FIG. 5 in which sectors 50 and 52 are shown rotatable about pivots 100 and 102 respectively.

Here it can be seen that fixed pins 80 are at the bottom of corresponding slots 82 in carriages 74 and 76. In this position the optical axis of the channels are parallel and focused at infinity. When however it is desired to focus into a spot between 6 and 60 inches from the binocular assembly, sectors 50' and 52' are rotated which causes objective lens support assembly 41 and 43 to move in the direction of arrows 110 and 112.

Simultaneously carriages 74 and 76 move in the direction of arrows 78 to move respective focal plane arrays 70 and 72 aft along the optical center line of the respective objective lens. This is due to the camming action of fixed pin 80 against slot 82 in each of the focal plane array carriages.

It is noted that carriages 41 and 43 are pivoted about pivot 100 and 102 respectively to skew the optical channels, with pivot 100 and 102 serving both for the pivoting of the sectors and the pivoting of the objective lens support assembly.

Figure 7:
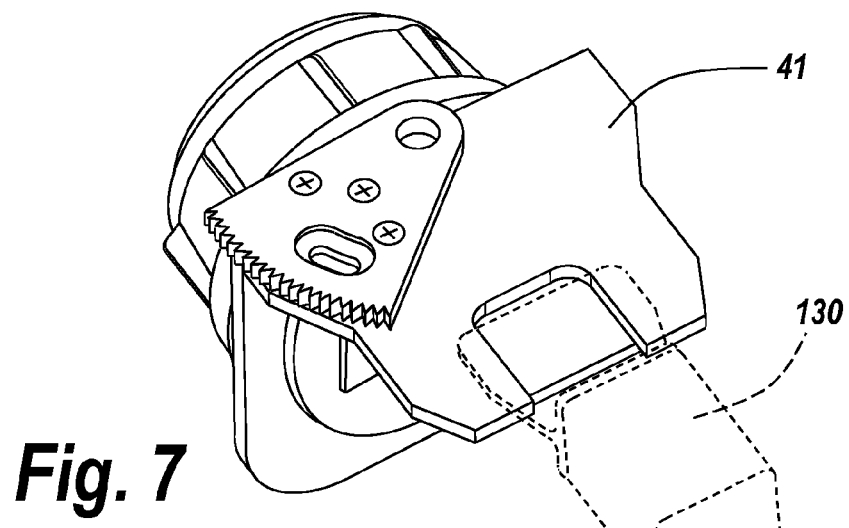
FIG. 7 is a diagrammatic illustration of the utilization of an autofocus module mounted to the carrier for the focal plane array which is used either in combination with the mechanical carriage adjustment of FIGS. 5 and 6 or independently thereof to provide proper positioning of the focal plane array with respect to the principal lens; and, FIG. 8 is a diagrammatic illustration of the two optical channels and a focal plane array on a carrier that is positioned utilizing a wheel alignment translational support system.

Referring now to FIG. 7, an objective lens support assembly in this case assembly 41, rather than being supplied with a translational carriage for the support of the moveable focal plane array is rather provided with an autofocus module shown in dotted outline at 130 which due to its automatic operation moves the associated focal plane array to automatically focus on the spot selected.

Figure 8:
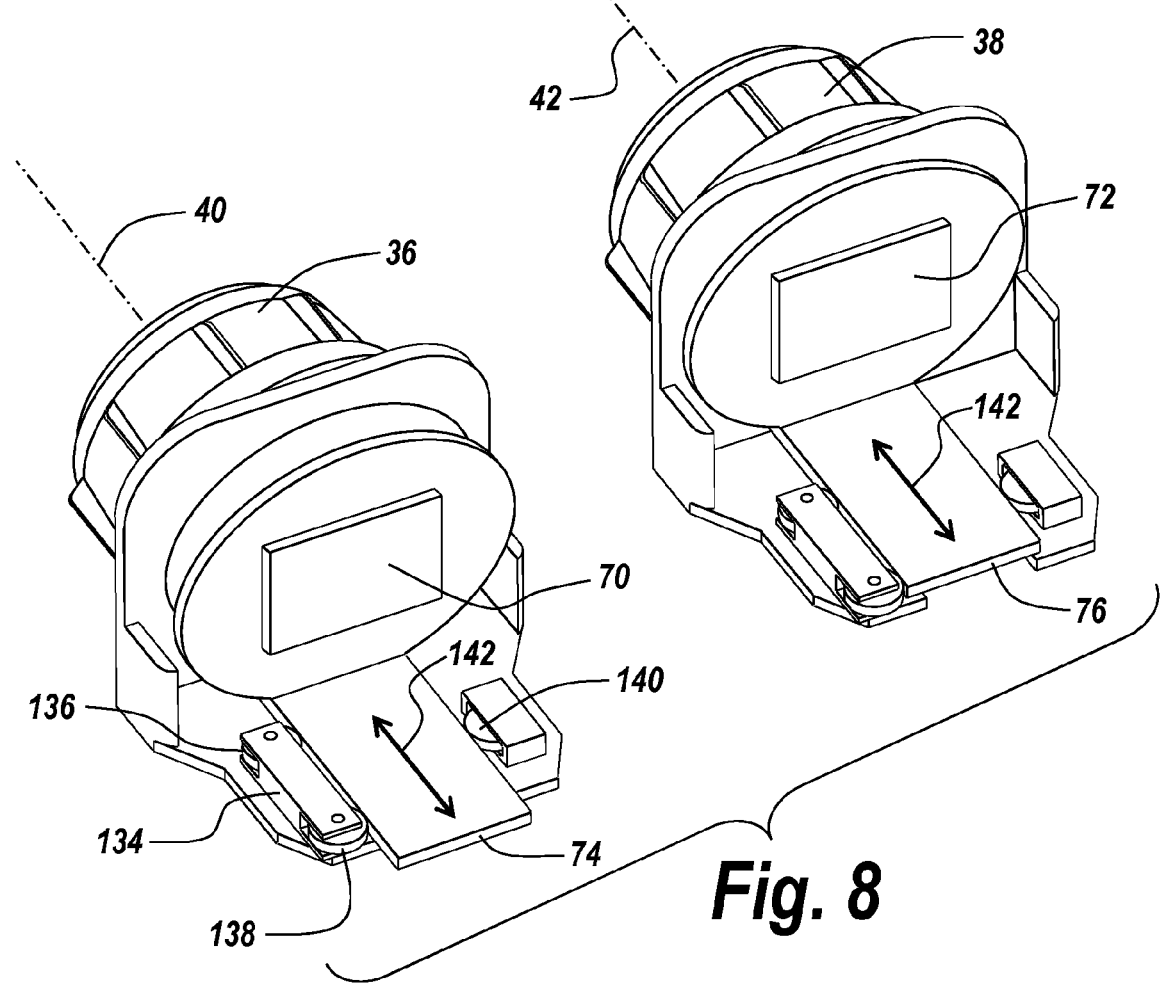

Referring now to FIG. 8, it can be seen that carriages 74 and 76 may be mounted for translation along the optical center line 40 and 42 of the objective lenses 36 and 38 by virtue of supporting the carriage with a roller wheel assembly here shown at 134 with two wheels 136 and 138 to one side of the carriage, whereas a single wheel 140 coacts with an opposite side of carriage 74 to maintain the movement of the focal plane array carriage in the direction of double ended arrow 142. Here the focal plane arrays 70 and 72 are shown mechanically attached to the respective translatable carriages 74 and 76 such that the focal plane array is moved in towards or away from the objective lens along the optical center line of the lens.

In summary, the subject system provides close in focusing of an infrared binocular camera unit by first skewing the optical center lines of the two optical channels so that they converge at a point close in to the binoculars, in one embodiment between 6 inches and 60 inches. Simultaneously with the skewing of the optical channels, the associated focal plane arrays are positioned at the focal point of the objective lenses in the binoculars so that the point to which the channels are skewed is in focus in each one of the channels. Thus the clarity or crispness of the infrared image is dependent on both the skewing of the optical channels to focus in on a close in point while at the same time adjusting the focal plane array positions relative to their objective lenses to provide the best possible focus.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A binocular infrared imaging system for close in focusing comprising: a pair of binoculars having optical channels including an objective lens that defines an optical center line for the channel; a pivotable assembly for skewing the center lines for the optical axes to intersect at a near in point in space; and, a focusing assembly for simultaneously focusing on said near in point as said channels are skewed to said near in point, wherein said pivotable assembly includes a pair of skewing gears each mechanically connected to a separate pivotable objective lens support and a focusing gear between said skewing gears operably engaging said skewing gears with the rotation thereof, thus to skew the optical center lines upon rotation of said focusing gear.

2. The apparatus of claim 1, wherein said near in point is a range from said binoculars of between 6 inches and 60 inches.

3. The apparatus of claim 1, wherein said pivotable assembly includes pivotable objective lens support for each channel.

4. The apparatus of claim 1, wherein said skewing gears includes sector gears, each having gear teeth along a periphery thereof.

5. The apparatus of claim 4, wherein each of said optical channels includes a focal plane array and wherein said focusing assembly includes a translating carriage for each of said optical channels for moving an associated focal plane array along the optical center line of the associated objective lens.

6. The apparatus of claim 5, wherein said carriage carrying a focal plane array is moved responsive to the skewing of the center lines of said optical channels.

7. The apparatus of claim 6, and further including a mechanical linkage between said skewing gears and respective carriages such that movement of said skewing gears results in moving of said carriages.

8. The apparatus of claim 7, wherein said mechanical linkage includes a pin-slot carrying assembly.

9. The apparatus of claim 7, wherein as said skewing occurs, each of said carriages moves the associated focal plane array away from the associated objective lens.

10. The apparatus of claim 5, and further including an auto focus module mechanically connected to a respective carriage for moving the respective carriage and the associated focal plane array so as to establish focus in the associated optical channel.

11. The apparatus of claim 5, wherein each of said carriages is made to translate along support rods mechanically affixed to associated objective lens supports.

12. The apparatus of claim 5, and further including a roller assembly for each of said carriages for permitting translation of said carriages with respect to associated objective lenses along respective center lines thereof.

13. The apparatus of claim 12, wherein said roller assembly includes wheels in a cage mechanically fixed to the associated objective lens support.

14. The apparatus of claim 1, wherein each of said optical channels includes a focal plane array.

15. The apparatus of claim 14, wherein said focal plane array has a 17 micron or less pixel spacing.

16. A method of providing sharp close in infrared images comprising the steps of: providing a pair of binoculars having infrared focal plane arrays in which the binoculars have optical channels having optical center lines that are skewed to intersect at a point in space close to the binoculars; and, moving the focal plane arrays with respect to associated objective lenses simultaneously with the skewing of the optical channels to provide a sharp focus in each of the channels, wherein the optical channels are skewed mechanically in accordance with a turn of a focus wheel and wherein the movement of the focal plane arrays is mechanically ganged to the focus wheel such that precision focus is obtained simultaneously when the focus wheel is used to skew the optical center lines of the channels to intersect at a close in point in space.

17. The method of claim 16, wherein the focal range for the binoculars is between 6 inches and 60 inches.

18. The method of claim 16, wherein each of the focal plane arrays has pixel spacing equal to or less than 17 microns.

* * * * *